(12) United States Patent
Russell

(10) Patent No.: US 9,128,043 B2
(45) Date of Patent: Sep. 8, 2015

(54) REFERENCE ELECTRODE AND COMBINED ELECTRODE

(76) Inventor: Timothy Russell, Kedah (MY)

( * ) Notice: Subject to any disclaimer, the term of this patent is extended or adjusted under 35 U.S.C. 154(b) by 590 days.

(21) Appl. No.: 13/265,617

(22) PCT Filed: Feb. 3, 2010

(86) PCT No.: PCT/GB2010/050166
§ 371 (c)(1),
(2), (4) Date: Jan. 5, 2012

(87) PCT Pub. No.: WO2010/122318
PCT Pub. Date: Oct. 28, 2010

(65) Prior Publication Data
US 2012/0098544 A1    Apr. 26, 2012

(30) Foreign Application Priority Data
Apr. 21, 2009  (GB) .................................. 0906828.9

(51) Int. Cl.
*G01N 27/416* (2006.01)
*G01N 27/401* (2006.01)
*G01N 27/30*  (2006.01)

(52) U.S. Cl.
CPC ............ *G01N 27/401* (2013.01); *G01N 27/301* (2013.01)

(58) Field of Classification Search
CPC . G01N 27/414; G01N 27/401; G01N 27/333; G01N 27/301; C12Q 1/6869
See application file for complete search history.

(56) References Cited

U.S. PATENT DOCUMENTS

| | | | |
|---|---|---|---|
| 3,671,414 A * | 6/1972 | Grubb | 204/414 |
| 3,672,962 A * | 6/1972 | Frant et al. | 205/786.5 |
| 3,957,613 A * | 5/1976 | Macur | 204/412 |
| 4,519,891 A | 5/1985 | Sugahara et al. | |
| 4,774,029 A | 9/1988 | Poulin | |
| 4,990,581 A | 2/1991 | Poulin | |
| 5,230,786 A | 7/1993 | Preidel | |
| 2002/0148737 A1 | 10/2002 | Haaf | |

FOREIGN PATENT DOCUMENTS

| | | |
|---|---|---|
| EP | 0068025 A1 | 1/1983 |
| GB | 1371888 A  | 10/1974 |
| WO | 9315393 A1 | 8/1993 |

\* cited by examiner

*Primary Examiner* — Minh N Tang
(74) *Attorney, Agent, or Firm* — Fox Rothschild LLP; Peter J. Butch, III

(57) ABSTRACT

A reference electrode including an outside wall which acts as a boundary between electrolyte and sample solution, which outside wall includes a resin which is ionically conducting, non-porous and salt-loaded, and a barrier through which no electrochemical communication between the electrolyte and sample solution is possible. A window is present in the barrier, allowing electrochemical communication between the electrolyte and the sample solution through the resin at the window. The reference electrode can be suitable for use with a separate measuring electrode, or can be combined with a measuring electrode in a single unit electrode assembly.

14 Claims, 2 Drawing Sheets

REFERENCE ELECTRODE AND COMBINED ELECTRODE

CROSS-REFERENCE TO RELATED APPLICATIONS

This application is the 35 U.S.C. §371 National Phase Application of International Application Serial No. PCT/GB2010/050166, filed Feb. 3, 2010, which claims priority to GB Application No. 0906828.9, filed Apr. 21, 2009, the disclosure of which are hereby incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB).

Not Applicable.

BACKGROUND OF THE INVENTION

The present invention relates to a reference electrode and to a combined electrode comprising a reference electrode and a measuring electrode.

A combined electrode contains both a reference electrode and a measuring electrode in one unitary measuring member. Many applications utilize the reference electrode and the measuring electrode in one unit because this is compact and convenient. Nevertheless a separate reference and measuring electrode can be used, and the present invention relates to improvements in a reference electrode regardless of whether this is separate or part of a combined electrode.

Reference electrodes are used together with measuring electrodes in electrochemical systems to determine the concentration of ions in a sample, e.g. the pH or pX where X represents an ion. The electrochemical potential of the reference electrode should remain as constant as possible throughout the measuring process while the potential of the measuring electrode, which can be ion-selective, is a function of the concentration of the ion being tested in the sample. The potential of the reference electrode is kept substantially constant due to the presence of a saturated electrolyte salt bridge within the cell. The potential difference between the reference electrode and the measuring electrode is indicative of the concentration of the ion and may be displayed on a millivolt instrument such as a potentiometer.

The potential of the complete electrochemical cell made up of the measuring electrode and the reference electrode can be represented by the following equation:

$$E_{Cell} = E_{meas} + E_{ref} + E_j$$

where $E_{meas}$ is the potential of the measuring electrode, $E_{ref}$ is the potential of the reference electrode and $E_j$ is a junction potential.

The junction potential arises from the different rates of mobility of anions and cations at the interface between two electrolytic solutions. Ideally, the junction potential of the reference electrode should have a negligible variation between solutions as otherwise the change in the junction potential will appear as an error in the overall potential calculated for the sample and hence the concentration determined.

Thus, where pH is being measured, a reference electrode ideally produces a constant millivolt potential in all aqueous liquids regardless of whether this be pure water, oily water, contaminated water or otherwise. A measuring electrode produces a different potential depending on the pH of the solution. Thus, using both electrodes together allows an accurate determination of the pH of a solution, taking into account a baseline measurement.

Well-known reference electrodes include the Ag/AgCl type and the calomel type amongst others; any convenient half-cell of electrode and electrolyte can be used in reference systems.

Some conventional reference electrodes require the electrolyte to leak slowly through an opening in the reference electrode, for example at a porous plug (e.g. made from wood or teflon or other porous materials), to form a liquid junction between the salt bridge and the sample solution being tested. In certain applications, a precipitate can form at the junction of the reference electrode and the sample solution where the electrolyte of the reference electrode flows into the sample. This precipitate can clog the opening and therefore interfere with the liquid junction potential and give rise to measuring errors. Furthermore, porous electrodes are prone to fouling, poisoning or back-diffusion of medium, and also lack robustness in the presence of temperature and pressure variations.

The problems associated with porous reference electrodes have previously been addressed by using a salt-loaded resin to surround the electrode chamber so as to provide a barrier to liquid movement whilst ensuring electrochemical communication. Such a system is described in for example WO 93/15393 of Amagruss Limited and Russell. Thus, the problems of porous reference electrodes can in part be avoided by using said salt-loaded resins instead of porous members. Such ionically-conducting salt-loaded resins cannot be poisoned because there is no liquid contact and furthermore the materials are steam sterilizable at 130 degrees C. and able to withstand pressures above 30 bar.

Nevertheless, further improvements of measurement accuracy and reliability are desirable.

BRIEF SUMMARY OF THE INVENTION

From a first aspect the present invention provides a reference electrode for use with a measuring electrode for measuring ion activity in a sample solution, said reference electrode comprising an electrode chamber for holding electrolyte and an electrode element in said electrode chamber, the outside wall of said reference electrode, in use, acting as a boundary between the electrolyte and the sample solution, and comprising a resin which is ionically conducting, non-porous and salt-loaded, and a barrier through which no electrochemical communication between the electrolyte and sample solution is possible, wherein a window is present in said barrier thereby allowing electrochemical communication between the electrolyte and the sample solution through the resin at said window.

Thus, whilst preserving the benefits of using an electrochemically conducting, salt-loaded resin, the present invention provides the additional advantage of limiting the area of contact between the electrolyte and the sample solution to a specific portion of the reference electrode, thereby allowing greater control and accuracy. Defining the electrochemically conducting region by the window of a barrier allows a convenient manufacturing method. The use of the barrier material allows convenient shielding of certain areas of the resin and of the electrode chamber.

The electrode may for example take the form of an elongate member which is designed to be partially immersed or dipped into a sample solution. This is perhaps the commonest shape of electrodes, and typically includes a body which is generally cylindrical in the body with a rounded or tapered end.

The reference electrode may be a tubular form, which may be an open tube or a tube closed at one end.

The electrode does not need to be of the elongate kind which is designed to be partially immersed or dipped into a sample solution. Other forms are possible and compatible with the present invention. For example the electrode may be a "flowthrough" electrode or an electrode which is designed to be completely immersed or form part of a larger apparatus. It is still advantageous in these other variants to have a window which confines the area of electrochemical communication.

Various configurations of the resin and the barrier within the outside wall are possible. For example, the barrier may be an innermost layer, so that it can face the electrolyte except at the location of the window (where the barrier is not present), and the resin may be an outermost layer, so that it can be shielded from the electrolyte except at the window. This is compatible with a particularly effective manufacturing process wherein barrier sleeve(s) or tube(s) may be temporarily push-fitted onto a cylindrical core, and then the resin may be allowed to cure between said barrier sleeve(s) (and said core) and an outer form or mold. The window then occurs at the point where no barrier sleeve was present over said core. The resin and barrier are preferably of materials which can bind together, for example by curing of the resin onto the barrier.

The core can be any inert material, for example a silicone tube, e.g. a 6 mm outside diameter standard silicone cord or tube (e.g. 60 shore hardness) commercially available from Silex Ltd, Bordon, Hampshire, UK. The core may be solid. Alternatively the core may be hollow except at its base; this has the additional advantage that the core is more elastic, flexible and can be elongated. Instead of silicone, any other inert material may be used, for example rubber tubing or neoprene core. Suitable materials do not bond to the inert barrier material or the resin. Preferably the core has surface properties such that the barrier and the resin can be easily removed.

The form or mold can for example be test-tube shaped and optionally made from glass. Cylindrical glass structures can be made on a lathe and then the end (destined to be the base) can be melted to form a conus closure. An example of a suitable size is approximately 14 mm outside diameter (or 8 to 25, or 10 to 20 mm) and 1 mm thick (or 0.5 to 2 mm).

The barrier and the resin bind well together; one way of achieving this is to use the same composition (minus the salts) for the barrier and the resin. The barrier and the resin may be coloured differently; this eases quality control and facilitates visualization of the location of both, and therefore easy visualization of the location of the window.

The outside wall of the reference electrode may have other components as well as the barrier and the resin. For example, where the reference electrode is a separate reference electrode designed to be used with a separate measuring electrode, then seals, for example O-ring seals could be used to seal around the point of entry of the electrode element at the top of the electrode.

Other components may also be present; for example where the resin is an outer layer and the barrier is an inner layer, there may be yet further components or layers on the outside or inside, so long as these do not adversely affect the functioning of the electrode.

The window may for example take the form of an annular or ring shape. Alternatively other shapes are possible and suitable; for example the window may take the form of holes, e.g. round or drilled holes, in the barrier.

In a reference electrode designed to be used with a separate measuring electrode, as shown for example in FIG. 1 below, the window through which electrochemical communication may occur, may for example be a portion of the lower ("wet" when in use) end of the electrode. For example, in the bottom 5—40 mm of the electrode, the wall between the electrolyte and the sample solution may comprise the resin but not the barrier.

It should be noted that, whilst the standalone reference electrode in FIG. 1 has a window bounded only at its upper end, the invention also covers all other forms of window in both standalone and combined electrode forms, including for example windows which are bounded on upper and lower boundaries, e.g. annular or ring-shaped windows, and other shapes including for example holes, e.g. round or drilled holes, in the barrier.

In a further aspect of the present invention, as shown for example in FIGS. 2 and 3 below, the reference electrode is combined with a measuring electrode to form a single-unit electrode assembly.

For example, the reference electrode may take the form of a sleeve around the measuring electrode, with the measuring electrode bulb extending beneath the sleeve.

The combined electrode may take the form of an elongate member wherein the measuring electrode is positioned centrally along the longitudinal axis and the reference electrode chamber takes the form of a sleeve, of annular cross-section, around said measuring electrode.

In one aspect of this combined electrode form, the reference electrode is annular in cross-section and the radially inner wall of the reference electrode chamber may be the radially outer wall of the measuring electrode chamber and take the form of a tube with the measuring electrode member fitted along the longitudinal axis. There is of course no communication across the boundary between the reference electrode and the measuring electrode, and the measuring electrode operates in a conventional way, allowing measurement through its bulb. The annular reference electrode chamber may be bounded on its radially outer surface by the outside wall previously mentioned, on its radially inner surface by the outer wall of the measuring electrode, and at its top and bottom ends by seals, for example O-ring seals.

Thus, in this embodiment, the measuring electrode is fitted inside a tube of the outside wall of the reference electrode so as to define an annular reference electrode chamber between them to hold reference electrolyte, with the measuring electrode as the radially-inner wall and the tube of the outside wall of the reference electrode as the radially outer wall of the chamber, and a reference electrode element housed in said chamber.

Thus the window in the boundary part of the reference electrode can be provided part way up the reference electrode part of the combined electrode.

For example, the top of the contact window in the reference electrode and the bottom of the tip of the measuring electrode bulb can be in close proximity, for example within 40 mm, 30 mm or 20 mm. The size of the contact window (i.e. from the top of the contact window to the bottom of the contact window) may be approximately 2 mm to approximately 15 mm, for example 5 mm to 10 mm.

The ionically conducting salt-loaded resin component of the outer wall of the reference electrode, which is approximately cylindrical in shape, may for example conveniently be made by one of two methods. The material may be cast into a vertical tube, or it may be made by a horizontal method which involves spinning the tube. The horizontal method results in an even distribution of salt along the length of the tube, but most of the salt concentrates towards the outer surface. In contrast, the vertical method results in a greater concentration of salt at the bottom ("wet") end of the tube. This is advantageous, because it is desirable to have a large salt concentration at the wet end of the tube in order for the resistance (impedance) to be low, but there is however a gradient of salt content and hence a gradient of resistance along the length of the tube by this method. This can result in immersion errors which can cause readings to vary depending on the extent to which the electrode is immersed in the medium. Therefore it is particularly advantageous for the contact window to be at or near the lower ("wet") end of the reference electrode. Preferably the contact window is within 5 cm, for example within 4 cm, or within 3 cm, of the bottom of the electrode.

The resin is an immobilized non-porous polymer having one or more salts of potassium, sodium and/or lithium mixed through before curing of the polymer to render it electrically conductive. The resin provides a physical barrier between the electrolyte and the sample solution but permits electrochemical communication between them. The salt(s) in the resin form part of the salt bridge of the reference electrode. No glass tube is required to hold the electrolyte. It is not necessary for the resin to contain dispersed silver chloride.

The electroconductive wall material preferably comprises a polymeric support containing dispersed salts selected from chloride, nitrate, sulphate and bromide salts of potassium, sodium and/or lithium. A major proportion of a potassium salt with a minor proportion of a lithium salt is preferred (e.g. in a ratio from 8.5:1 to 9.5:1), the presence of lithium being advantageous to reduce the resistance and thus to reduce response time for the electrode. Hygroscopic salts, e.g. LiCl, are also advantageous because they prevent the outside surface of the electrode wall from dehydrating and therefore have a protective effect in maintaining the conductivity properties of the electrode The polymers useful in the wall material of the present invention should themselves have good electrochemical insulation properties, e.g. vinyl ester resins, polyesters, polyethylene, polypropylene, polyvinyl chloride or epoxy resins. The vinyl ester resins are preferred because of their chemical resistance. The polymers are cured under conventional conditions for the respective polymers to form a solid, immobilised non-porous body containing the salt(s) dispersed therethrough.

Typical curing conditions are 10 minutes to 48 hours, e.g. overnight at room temperature or from 10 to 60 minutes at a temperature of between 40 and 100 degrees C. Epoxy resins curable by ultraviolet light may also be suitable.

Typically the wall material comprises from 35-55% by weight of salt(s) dispersed in from 55-35% by weight of polymer resin, preferably about 50% resin and about 50% salts, so that the salt(s) is/are densely dispersed throughout the material (the percentages being based on the total weight of the composition). At the base of the cured material, in the vicinity of the window, the salts form a higher percentage of the material (generally greater than 50%). The preferred resin/KCl ratio is about 48/44 by weight as this produces a good curing mix and a high KCl concentration. Additives such as initiators and accelerators used in promoting the curing process may be present in small amounts. In cases where the wall material acts as a protective cover surrounding a silver halide containing cell (e.g. an Ag/AgCl electrode) it is advantageous that the protective cover be opaque so as to prevent photodegradation. To achieve this, graphite or other colourants may be dispersed in suitable amounts in the composition.

The wall material in tubular form may be manufactured by molding or spinning techniques, for example by spinning during curing, e.g. by spinning about a horizontal axis. Preferably however the wall material may be molded and then left standing vertically during curing so that the salt concentration tends to increase in the lower region. If the salt is of relatively high molecular weight (e.g. $KNO_3$), a high proportion of the salt may settle in the lower region until that lower region is saturated (or loaded to full capacity) with the salt.

The present invention thus addresses the problems of immersion errors whilst retaining the advantages of using ionically conducting salt-loaded resins and in particular those made by the vertical casting method.

For example, the salt-loaded resin may be as described in the invention published as WO 93/15393 of Amagruss Limited and Russell.

The barrier is a material which blocks the area of contact between the electrolyte and the sample solution. The barrier may be an inert sleeve material which may be made, for example made, of epoxy resin, or other material which is non electrochemically active.

There may be a distinct window such that a barrier portion is present at the lowest part of the reference electrode and bounding the bottom of a contact window and further barrier portion is present and bounding the top of the contact window. The barrier may have the same base polymer composition as the resin, or may be a different inert material, so long as it bonds with the resin.

In an alternative configuration, as shown for example in FIG. 3 below, the barrier may be present along the outer surface of the reference electrode and the resin may form part of the base of the reference electrode chamber and provide a contact window at that point.

Thus, in this configuration, the measuring electrode is fitted inside a tube of the barrier which tube is sealed at its bottom end by a seal, for example an O-ring seal, and by a portion of the salt-loaded resin so as to define an annular reference electrode chamber between said barrier and said measuring electrode and to hold reference electrolyte, with the measuring electrode as the radially-inner wall and the tube of the barrier as the radially outer wall of the chamber, and a reference electrode element housed in said chamber.

The present invention will now be described by way of example only, and in further non-limiting detail, with reference to the following figures in which:

DETAILED DESCRIPTION OF THE INVENTION

Figure 1:
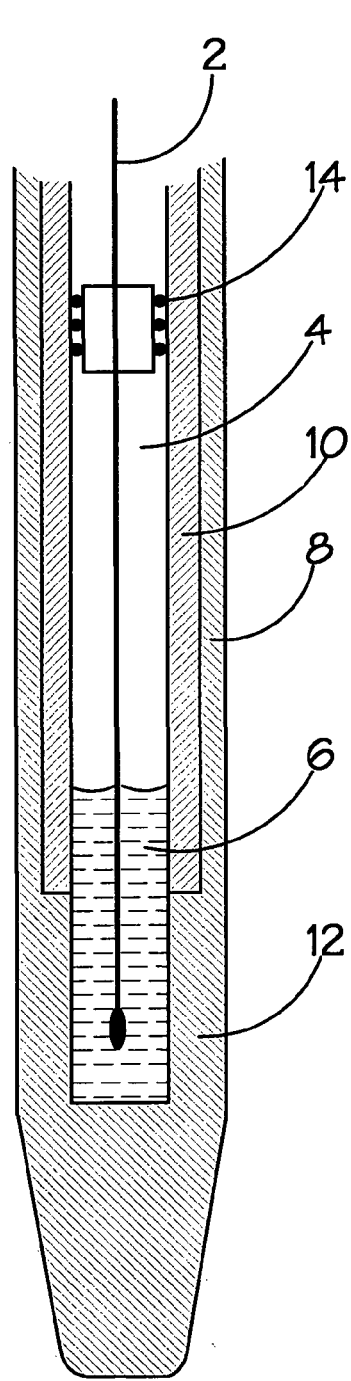
FIG. 1 shows, not to scale, a diagrammatic longitudinal cross-sectional representation of a reference electrode in accordance with the present invention.
Figure 2:
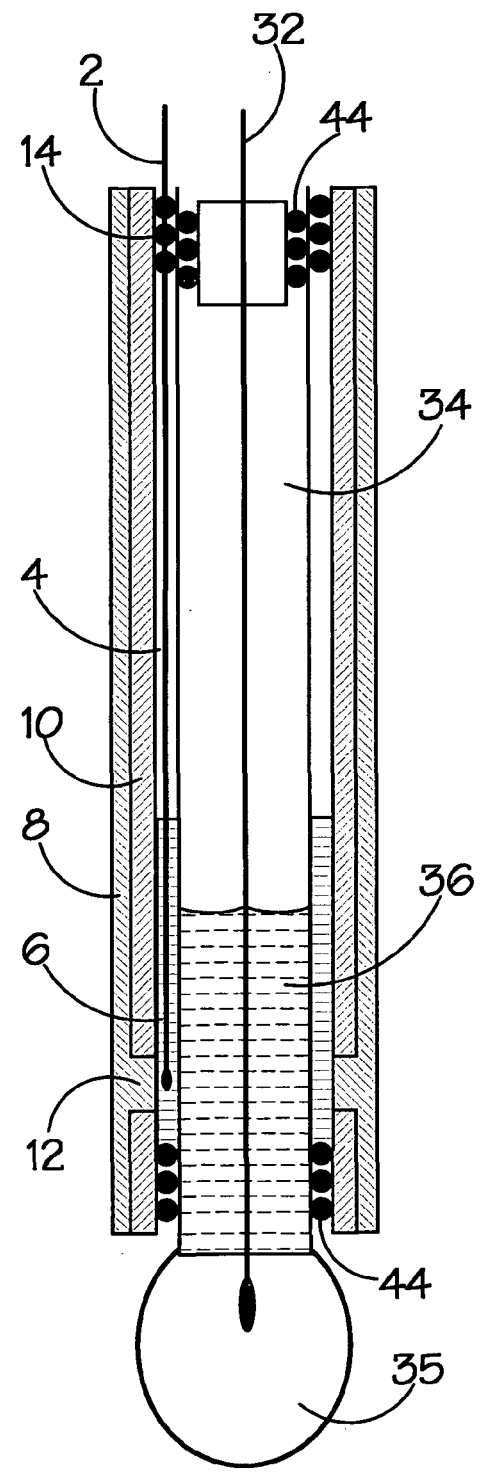
FIG. 2 shows a representation of a combination electrode in accordance with the present invention.
Figure 3:
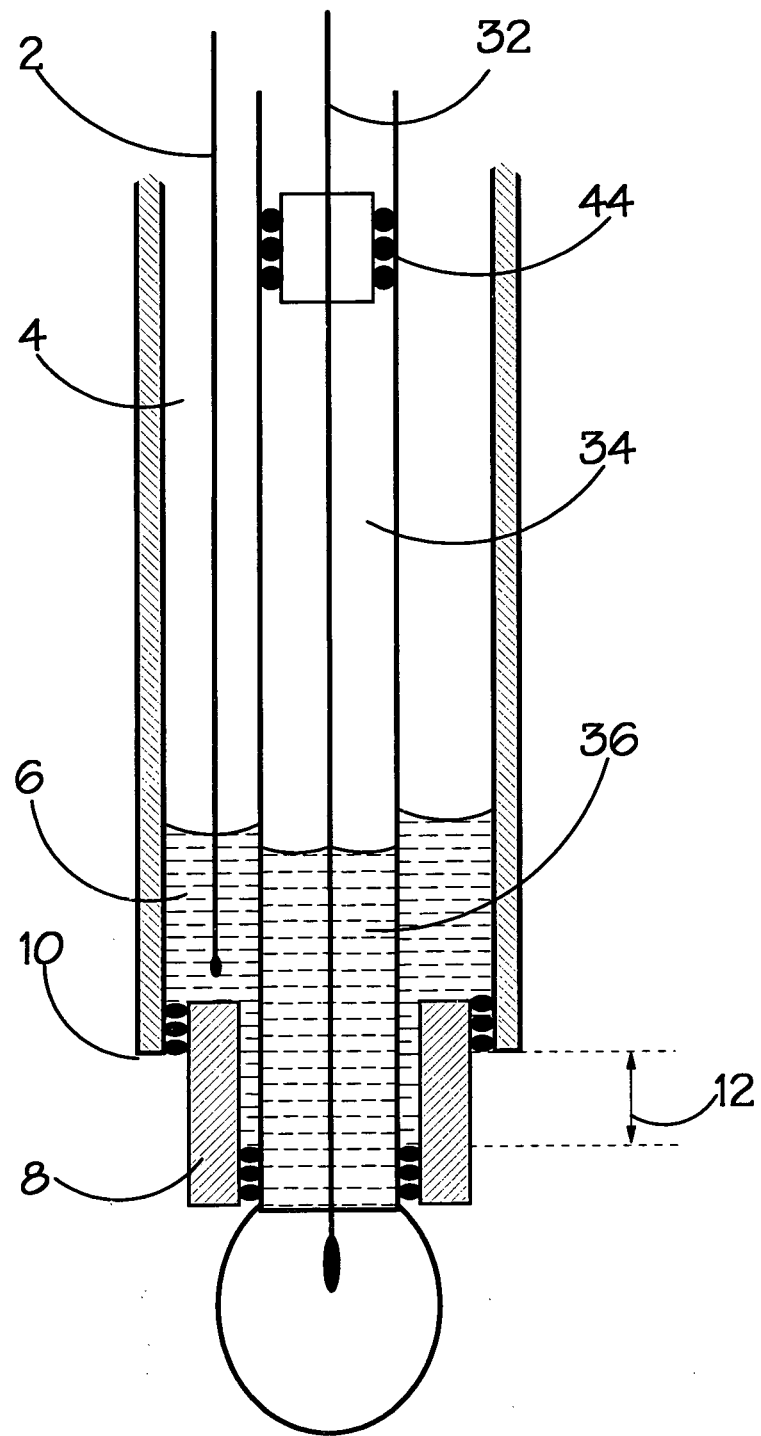
FIG. 3 shows a representation of a further combination electrode in accordance with the present invention.

In each of FIGS. 1, 2 and 3, a reference electrode element 2 is housed in a reference electrode chamber 4 which holds reference electrolyte solution 6; and the outside wall of the reference electrode chamber 4 comprises a resin 8 which is ionically conducting, non-porous and salt-loaded, and a barrier 10 through which no electrochemical communication between the electrolyte 6 and sample solution (not shown) is possible. The reference electrolyte 6 and sample solution can electrochemically interact through contact window 12. O-ring seals 14 are provided to seal around the point of entry of the reference electrode element 2 into the top of the reference electrode chamber 4.

FIG. 1 shows a reference electrode which is designed to be used with a separate measuring electrode.

FIGS. 2 and 3 however show a combined electrode comprising, in addition to the reference electrode, a measuring electrode. In FIGS. 2 and 3, measuring electrode element 32 is housed within a conventional measuring electrode chamber 34 which holds electrolyte 36 and comprising bulb 35, O-ring seals 44 are provided to seal around the point of entry of the measuring electrode element 32 into the top of the measuring electrode chamber 34. The measuring electrode is an elongate member comprising a cylindrical measuring electrode chamber 34 connected to bulb 35 and the reference electrode takes the form of a sleeve which fits around the cylindrical measuring electrode chamber so that the inside wall of the reference electrode is the outside wall of the measuring electrode. The top and bottom of the reference electrode chamber is sealed, in the embodiments shown, by O-ring seals 44.

FIGS. 2 and 3 show two of the possible configurations of the contact window 12. In both cases, the outside wall of the reference electrode chamber 4 comprises only resin 8, barrier 10 and seals 44.

In FIG. 2, barrier 10 extends along the entire length of the innermost surface of the outside wall, except for a ring-shaped portion (the window 12) a short distance from the bottom. Resin 8 extends along the entire length of the outermost surface of the outside wall and also into the contact window 12.

In FIG. 3, barrier 10 extends along the length of the reference electrode chamber 4. Resin 8 takes the form of a sleeve which fits over the measuring electrode chamber 34 and together with seals 44 forms the base of the reference electrode chamber 4 in an area which is not surrounded by barrier 10 and hence able to function as contact window 12.

The combined electrode illustrated in FIG. 2 may be manufactured according to a vertical casting method using spotlessly clean cylindrical glass test-tubes with tapered rounded ends. On a cylindrical core of diameter 7 mm are pushed a 1 cm sleeve and a 12 cm sleeve of epoxy barrier material. The epoxy barrier material is 1 mm thick. The 1 cm sleeve is pushed to the bottom of the core, then there is a gap of 7 mm until the base of the second sleeve. The core, onto which has been pushed the two epoxy sleeves, is then placed in an approximately test-tube shaped glass form which acts as a mold and which has a spotlessly clean inner surface, and into which has previously been charged salt-loaded resin-forming material. The salt-loaded resin-forming material is displaced into the space between the inner surface of the glass mold and the sleeved core. The material is allowed to cure. Heat is then applied to ease the removal of the hardened material from the glass form. The core is then removed to leave the composite material which can function as a window-containing outside wall of a reference electrode chamber. The bottom of the formed material (for example most of the tapered part) can be cut away to leave an over-sized sleeve which can be placed over a measuring electrode in the combined electrode embodiment.

The salt-loaded resin may in one example be about 1 mm thick (in the cylindrical part) as a layer outside an approximately 1 mm thick epoxy barrier inner layer. Of course, where the epoxy barrier is not present, i.e. at the window, the salt-loaded resin layer will then be approximately 2 mm thick in this example. Furthermore, where the bottom is not cut away (e.g. when forming a separate reference electrode for use with a separate measuring electrode, the bottom of the formed material in the vicinity of the curved end may contain a thicker salt-loaded resin part due to there being a larger gap between the cylindrical core and the glass form during vertical casting.

The overall diameter of the cylindrical part may for example be between 10 and 20 mm, for example approximately 12 mm or approximately 16 mm. The following electrodes have been prepared and are intended to be specifically covered by the present application: (i) a combined reference electrode of the type shown in FIG. 2 with diameter 12 mm; (ii) a combined reference electrode of the type shown in FIG. 2 with diameter 16 mm; (iii) a combined reference electrode of the type shown in FIG. 3 with diameter 12 mm; and (iv) a single reference electrode of the type shown in FIG. 1 with diameter 12 mm designed to be used with a separate measuring electrode.

This vertical casting of the resin/salt mix results in a salt gradient—the salts falling through the polymer due to weight—with the highest salt concentration being at the rounded end in the glass form. This salt gradient also is an impedance or resistance gradient—the impedance or resistance across the salt-containing polymer at the rounded end being approximately 50 K Ohms or less and at the top open end of the electrode being in the M Ohm range.

The introduction of the inert epoxy inner tube with a contact window at the wet (rounded or tapered) end confines the reference electrolyte contact with the electrochemically active polymer (<50K Ohm) to this contact window only. This eliminates the mV immersion error that occurs when the reference electrolyte is in contact with the entire inside polymer surface; this error occurs due to the salt/impedance gradient.

The ionically conductive hard polymer has replaced the need for the porous liquid-junction in reference electrodes. The porous liquid junction of the prior art has been associated with several problems, including issues resulting from sensitivity to temperature and pressure, or poor chemical resistance and liability to fouling/poisoning. The salt-loaded resin replaces the need for a porous liquid junction, acts as an immobilized hard non-porous ionically conducting electrolyte, and forms a separating interface preventing any liquid contact between the internal KCl electrolyte and Ag/AgCl (for example) and the water under test. This interface is pressure and temperature resistant and steam sterilizable and prevents any fouling/poisoning of the Ag/AgCl reference element (for example) and electrolyte, due to preventing liquid contact.

Thus the present invention in one aspect involves the vertical casting of the salt-containing conducting material in a glass (or other) form and the introduction of the isolating inert tube (e.g. epoxy) running along the inside length of the electrode; with the electrolyte contact gap at the low impedance/high salt wet end of the electrode. This eliminates the mV immersion error found with earlier electrode designs.

EXAMPLE 1

In one example, the electroconductive wall material may be produced as follows.

Potassium chloride is dried for 1 hour at 1500 degrees C. and then placed in a mill and ground to a fine powder. Lithium chloride is treated in a similar manner. The powdered salts (potassium chloride 90 g, lithium chloride 10 g) are added along with optionally 2 g of black graphite powder to a vinyl ester resin (100 g) and mixed thoroughly at 250 degrees C. A filler such as quartz may also be added for mechanical strength, typically in the amount of 5 g although this can be varied.

Prior to curing the following are added to the mixture (percentages are by weight of total composition): 1.5-2.0% Methyl ethyl ketone peroxide (initiator), 0.2-3.0% Cobalt octoate (accelerator), 0.5-2.0% Dimethylaniline (accelerator), 1.0-2.0% BYK-A515 (air release agent) (BYK-Chemie GmbH).

One particular example of the total composition is as follows (percentages by weight): Vinyl ester resin 48, KCl 44, LiCl 5, Graphite 1, Methyl ethyl ketone peroxide 1, Cobalt Octoate 0.5, Dimethylaniline 0.5. BYK A-515 0.5.

The mixture is then heated to 400 degrees C. for 10 minutes. Alternatively, the mixture can be allowed to cure at a warm ambient temperature overnight. The glass form is allowed to stand vertically during curing. A tube closed at the bottom may be formed in this way. The tube of the cured immobilised composition is rigid and self-supporting. It is not porous to electrolytic solutions. If desired, the internal and/or external surface of the tube may be abraded lightly to remove a surface film of polymer and expose the salt content.

The invention claimed is:

1. A reference electrode for use with a measuring electrode for measuring ion activity in a sample solution, comprising:
    an electrode chamber for holding electrolyte and an electrode element in said electrode chamber,
    an outside wall of said reference electrode, providing a boundary between the electrolyte and the sample solution, wherein said outside wall comprises
    a resin layer which is ionically conducting, non-porous and salt-loaded, and
    a barrier layer through which no electrochemical communication between the electrolyte and sample solution is possible,
    wherein a window is present in said barrier layer thereby allowing electrochemical communication between the electrolyte in said electrode chamber and the sample solution through the resin layer at said window; and
    wherein said outside wall of said reference electrode is a polymeric material prepared by a method comprising:
    vertically orientating a mold which is substantially cylindrical and closed at its bottom end;
    casting a salt-containing uncured polymer into said mold;
    fitting one or more sleeve(s) of barrier material onto a central cylindrical inert core;
    placing said core, carrying said sleeve(s), substantially centrally into said mold, thereby displacing the salt-containing uncured polymer so that said salt-containing uncured polymer occupies a gap between said sleeve-carrying core and the internal surface of the mold;
    curing the polymer whilst said mold is in a position so that its longitudinal position is substantially vertical;
    removing the mold and the central cylindrical inert core;
    and optionally cutting off part of the base of the cured material.

2. A reference electrode as claimed in claim 1 wherein the outside wall of said reference electrode is in tubular form.

3. A reference electrode as claimed in claim 1 wherein said resin layer is an immobilized non-porous polymer having one or more salts of potassium, sodium and/or lithium mixed through said polymer before curing of the polymer to render it electrically conductive, said polymer providing a physical barrier between the electrolyte and the sample solution but permitting electrochemical communication between them.

4. A reference electrode as claimed in claim 1 wherein said resin layer is an electroconductive material containing one or more dispersed salts selected from the group consisting of chloride, nitrate, sulphate and bromide salts of potassium, sodium and lithium.

5. A combined electrode comprising a reference electrode as claimed in claim 1 and a measuring electrode in a single-unit electrode assembly.

6. A combined electrode as claimed in claim 5 in the form of an elongate tube wherein the measuring electrode is positioned centrally along the longitudinal axis and the reference electrode chamber takes the form of a sleeve, of annular cross-section, around said measuring electrode.

7. A combined electrode as claimed in claim 6 wherein the measuring electrode is fitted inside a tube on the outside wall of the reference electrode so as to define an annular reference electrode chamber between them to hold reference electrolyte, with the measuring electrode as the radially-inner wall and the tube on the outside wall of the reference electrode as the radially outer wall of the chamber, and a reference electrode element housed in said chamber.

8. A combined electrode as claimed in claim 7 wherein the base of the reference electrode chamber is sealed.

9. A combined electrode as claimed in claim 6 wherein the measuring electrode is fitted inside a tube of said barrier layer, which tube is sealed at its bottom end by a seal and by a portion of said resin layer so as to define an annular reference electrode chamber between said barrier layer and said measuring electrode and to hold reference electrolyte, with the measuring electrode as the radially-inner wall and the tube of the barrier layer as the radially outer wall of the chamber, and comprising a reference electrode element housed in said chamber.

10. A reference electrode as claimed in claim 1 wherein the reference electrode is an Ag/AgCl reference electrode.

11. A reference electrode as claimed in claim 1 wherein the resin layer comprises a vinyl ester polymer.

12. A reference electrode as claimed in claim 1 which is configured for measuring pH.

13. A method of making a polymeric material suitable for use as the outside wall of a reference electrode, comprising:
    vertically orientating a mold which is substantially cylindrical and closed at its bottom end;
    casting a salt-containing uncured polymer into said mold;
    fitting one or more sleeve(s) of barrier material onto a central cylindrical inert core;
    placing said core, carrying said sleeve(s), substantially centrally into said mold, thereby displacing the salt-containing uncured polymer so that said salt-containing uncured polymer occupies a gap between said sleeve-carrying core and the internal surface of the mold;
    curing the polymer whilst said mold is in a position so that its longitudinal position is substantially vertical;
    removing the mold and the central cylindrical inert core;
    and optionally cutting off part of the base of the cured material.

14. A method as claimed in claim 13 wherein the mold is test-tube shaped.

* * * * *